United States Patent [19]
Carter et al.

[11] Patent Number: 5,814,613
[45] Date of Patent: Sep. 29, 1998

[54] ANTIBIOTIC LL-E19020 GAMMA

[75] Inventors: Guy Thomas Carter, Suffern; David R. Williams, Stony Point; Joseph D. Korshalla, Pearl River, all of N.Y.

[73] Assignee: Roche Vitamins Inc., Parsippany, N.J.

[21] Appl. No.: 756,411

[22] Filed: Sep. 9, 1991

[51] Int. Cl.$^6$ .......................... A01N 43/04; A61K 31/71; C07H 15/24; C07H 3/06
[52] U.S. Cl. .......................... 514/25; 536/16.8; 536/18.1
[58] Field of Search ................... 536/16.8, 18.1, 536/17.9, 18.7, 53, 55, 115; 514/25, 23; 424/122

[56] References Cited

U.S. PATENT DOCUMENTS

| | | | |
|---|---|---|---|
| 3,872,072 | 3/1975 | Naito et al. | 536/16.8 |
| 4,704,276 | 11/1987 | Kantor | 424/122 |
| 4,705,688 | 11/1987 | Carter et al. | 424/122 |
| 4,968,493 | 11/1990 | Carter et al. | 424/122 |
| 5,077,277 | 12/1991 | Phillipson et al. | 514/25 |

FOREIGN PATENT DOCUMENTS

| | | | |
|---|---|---|---|
| 442783 | 8/1991 | European Pat. Off. | 424/122 |

OTHER PUBLICATIONS

Journal of Antibiotics, 42 (10), 1489–1493 (1989).
Journal of Chromatography, 484, 381–390 (1989).
Journal of Antibiotics, 41(10), 1293–1299 (1988).
Journal of Antibiotics, 41(10), 1300–1315 (1988).
Journal of Antibiotics, 39(10), 1361–1367 (1986).
Journal of Antibiotics, 42(1), 94–101 (1989).
Antimicrobial Agents and Chemotherapy, 33 (3), 322–325 (1989).
Program and Abstracts of the 27th Interscience Conference on Antimicrobial Agents and Chemotheraphy, No. 995, p. 270, New York, Oct. 4–7 1987.
G.T. Carter et. al., "LL–E19020X and β, Novel Growth Promoting Agents," *J. Antibiotics* 41:10 pp. 1511–1514, (Oct. 1988).

*Primary Examiner*—Gary L. Kunz
*Attorney, Agent, or Firm*—George W. Johnston; William H. Epstein; John P. Parise

[57] ABSTRACT

The invention provides an antibiotic designated LL-E19020 Gamma which is derived from the microorganism *Streptomyces lydicus* ssp. *tanzanius* NRRL 18036.

3 Claims, 4 Drawing Sheets

ANTIBIOTIC LL-E19020 GAMMA

BACKGROUND OF THE INVENTION

1. Field of the Invention

The invention relates to a new antibiotic designated LL-E19020 Gamma, to its production by fermentation and to a process for its recovery and purification.

2. Description of the Prior Art

Antibiotics LL-E19020 Alpha and LL-E19020 Beta are disclosed in U.S. Pat. No. 4,705,688, The Journal Of Antibiotics, 41(10), 1511–1514 (1988) and The Journal Of Antibiotics, 42(10), 1489–1493 (1989). Antibiotic LL-E19020 Alpha has a phenylacetate ester group attached at C-23 and has the structure:

Antibiotic LL-E19020 Beta has a phenylacetate ester group attached at C-24 and has the structure:

A process for purification of the antibiotic LL-E19020 Alpha by reversed phase HPLC purification is described in Journal Of Chromatography, 484, 381–390(1989). Antibiotics LL-E19020 Alpha and LL-E 19020 Beta are also useful for increasing the growth rate of meat producing animals and for treating respiratory disease, fowl cholera and necrotic enteritis as described in U.S. Pat. No. 4,704,276 and U.S. Pat. No. 4,968,493.

A related family of compounds, the phenelfamycins, is reported in The Journal Of Antibiotics, 41(10), 1293–1299 (1988); The Journal Of Antibiotics, 41(10), 1300–1315 (1988); The Journal Of Antibiotics, 39(10), 1361–1367 (1986); The Journal Of Antibiotics, 42(1), 94–101 (1989); Antimicrobiol Agents and Chemotherapy, 33(3), 322–325 (1989); and Program and Abstracts Of The 27th Interscience Conference on Antimicrobial Agents Chemotherapy, No. 995, p 270, New York, Oct. 4–7 1987.

SUMMARY OF THE INVENTION

Figure 1:
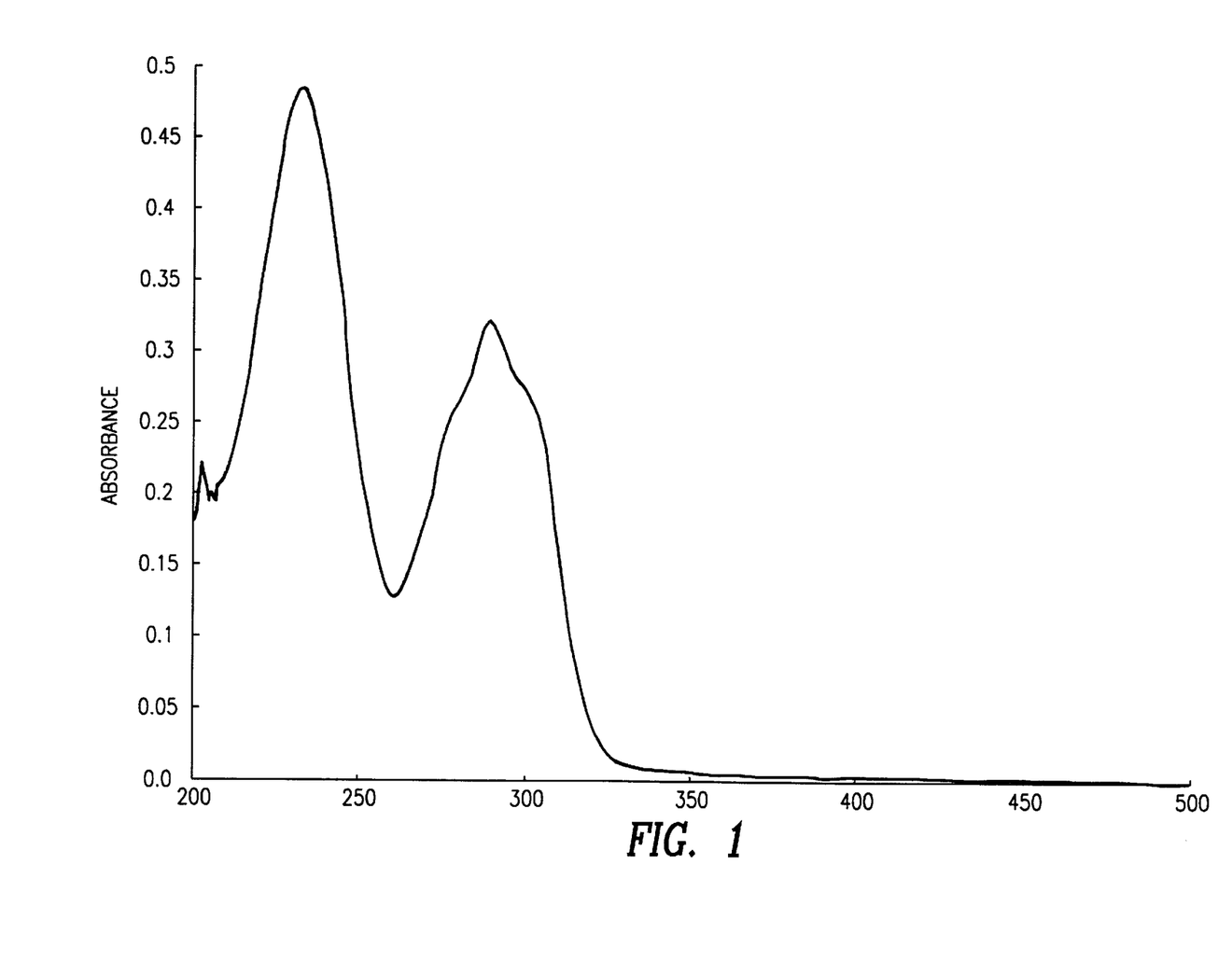
FIG. 1 shows the ultraviolet absorption spectrum of LL-E19020 Gamma.
Figure 2:
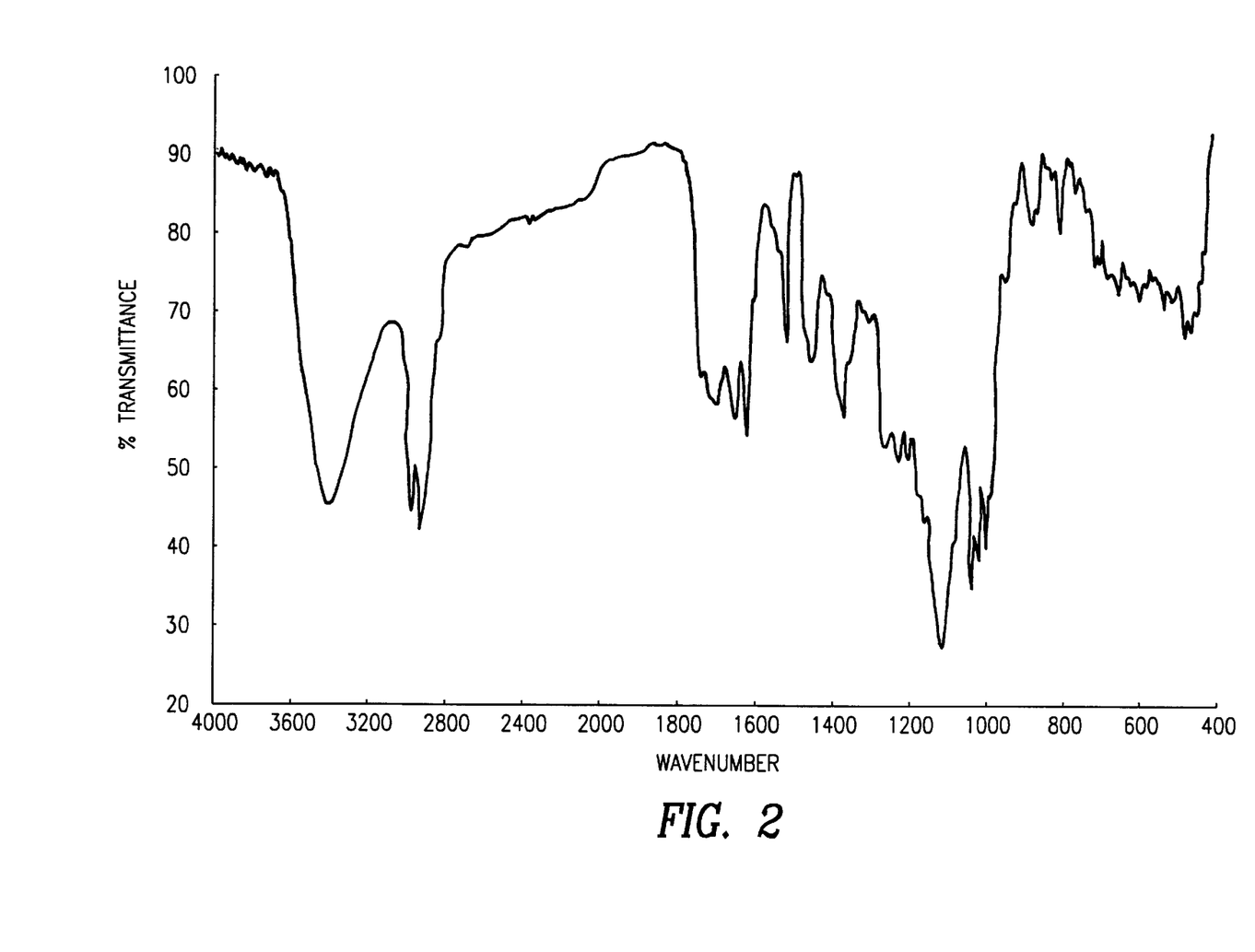
Figure 2 shows the infrared absorption spectrum of LL-E19020 Gamma.
Figure 3:
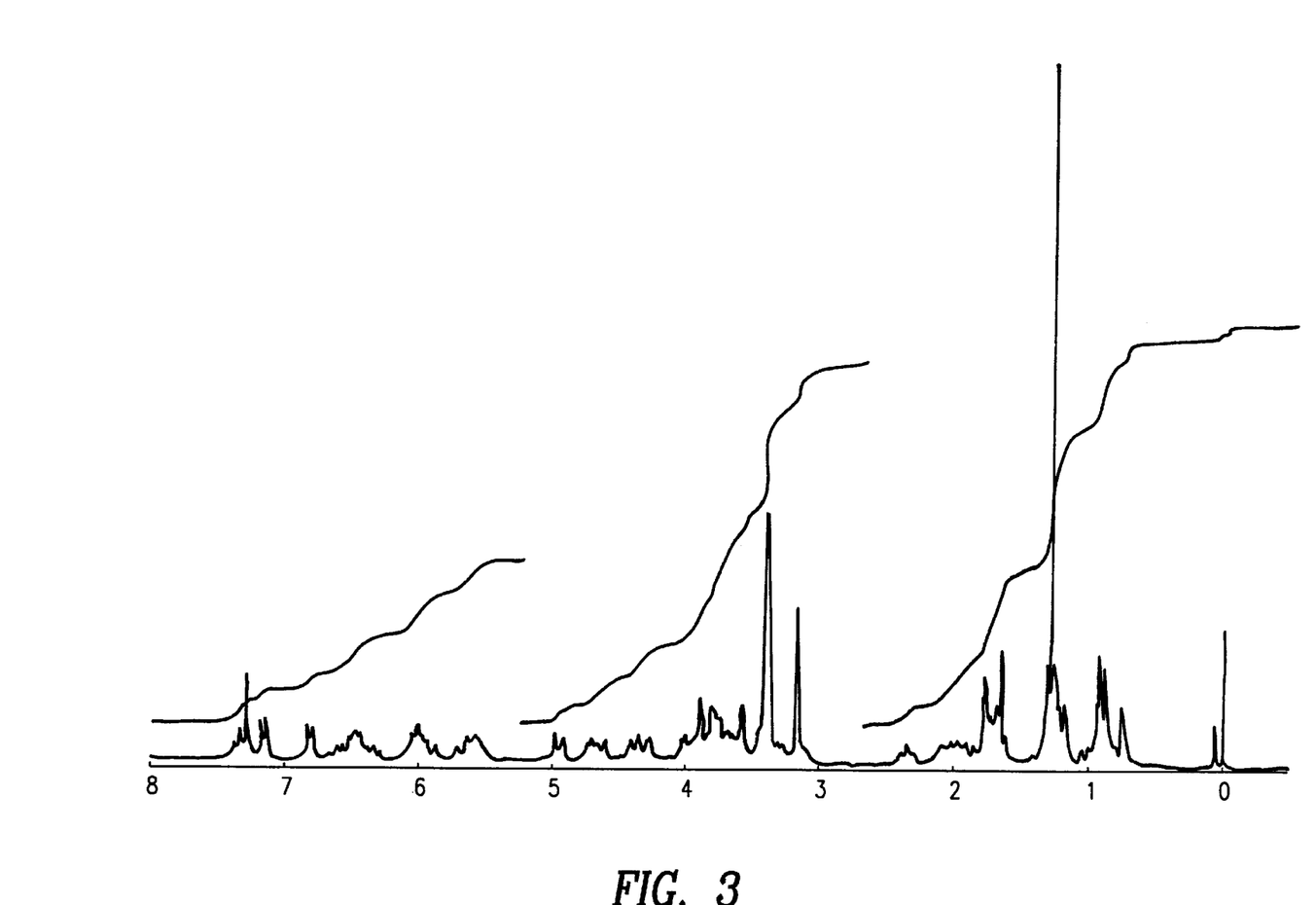
Figure 3 shows the proton nuclear magnetic resonance spectrum of LL-E19020 Gamma.
Figure 4:
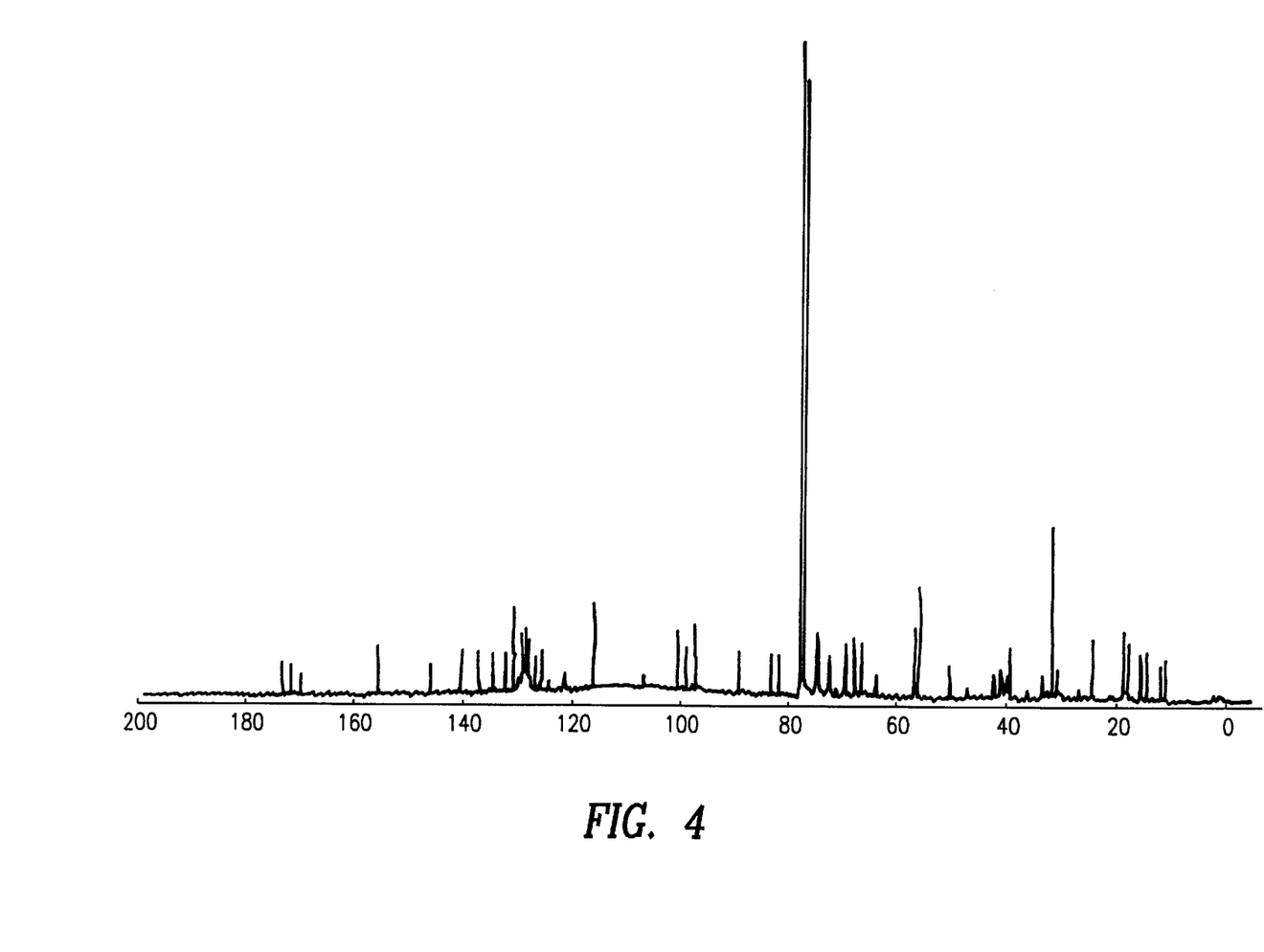
Figure 4 shows the carbon-13 nuclear magnetic resonance spectrum of LL-E19020 Gamma.

A new antibiotic designated LL-E19020 Gamma has now been found. The structure of the new antibiotic LL-E19020 Gamma is:

As can be determined from the above structure antibiotic LL-E19020 Gamma differs from the previously known antibiotics LL-E19020 Alpha and LL-E19020 Beta in that LL-E19020 Gamma has a 4-hydroxyphenylacetate ester group attached at C-23. The physico chemical characteristics of LL-E19020 Gamma are as follows:

1. Molecular weight:1241 (FABMS=M/Z 1264 corresponding to [M+Na]+)
2. Molecular formula:$C_{65}H_{95}NO_{22}$ microanalysis found (calc):C62.22(62.85); H7.77(7.66); N 0.92(1.13). HRFABMS:(M+K)+=M/Z 1280.5983 (calc. 1280.5983)
3. Specific optical rotation:$[\alpha]_D 26°$ C.=−7° C. (1.001, MeOH)
4. Ultraviolet Absorption Spectrum as shown in Figure I. UV absorption [MeOH]$\lambda$.max ($\epsilon$):231 nm (58,600); 287 nm (39,300).
5. IR absorption spectrum as shown in Figure II. IR absorption spectrum [KBr] $\nu$ max:3411br, 2974, 2934, 2828, 1735, 1716sh, 1700, 1652, 1647, 1617, 1455, 1367, 1222, 1098, 1023 $cm^{-1}$.
6. Proton $^1$H NMR[$CDCl_3$]:Spectrum (300 MHz) as shown in Figure III.
7. Carbon 13 $^{13}$C NMR[$CDCl_3$] Spectrum as shown in Figure IV, significant peaks listed below ($\delta$ from TMS):

| | | | |
|---|---|---|---|
| 173.4 | 127.5 | 74.64 | 49.77 |
| 171.9 | 126.3 | 74.51 | 41.85 |
| 170.1 | 125.1 | 74.42 | 40.92 |
| 155.7 | 120.7 | 74.07 | 39.91 |
| 145.7 | 115.6(2x) | 72.19 | 39.23 |
| 140.3 | 100.5 | 71.83 | 38.81 |
| 136.9 | 98.90 | 69.10 | 32.98 |
| 134.3 | 97.28 | 67.57 | 30.98 |
| 132.0 | 96.93 | 66.40 | 29.91 |
| 130.6(2x) | 89.16 | 66.07 | 23.75 |
| 130.1 | 83.21 | 63.57 | 18.10 |
| 129.0 | 81.64 | 56.53 | 17.20 |
| 128.5 | 77.63 | 56.10 | 17.00 |
| 128.3 | 77.20 | 55.50 | 14.84 |
| 128.2 | 76.46 | 55.45 | 13.50 |
| 128.1 | 10.97 | 10.18 | |

8. High pressure liquid chromatography (HPLC) retention time of 18.5 minutes using a gradient of acetonitrile in aqueous acetic acid.
9. High pressure liquid chromatography (HPLC) retention time of 19.6 minutes using a gradient of dioxane in aqueous acetic acid.

The new antibiotic LL-E19020 Gamma is formed along with LL-E19020 Alpha and LL-E19020 Beta during cultivation under controlled conditions of a strain of *Streptomyces lydicus* ssp. *tanzanius*, NRRL 18036. The new antibiotic LL-E19020 Gamma is separated from LL-E 19020 Alpha and LL-E19020 Beta and subsequently purified by high pressure liquid chromatography (HPLC).

DESCRIPTION OF THE PREFERRED EMBODIMENTS

The antibiotic LL-E19020 Gamma is produced by fermentation of a strain of *Streptomyces lydicus*, ssp. *tanzanius*, NRRL 18036, in an aqueous nutrient medium containing assimilable sources of carbon and nitrogen under submerged aerobic conditions. This microorganism is maintained in the culture collection of the Medical Research Division, American Cyanamid Company, Pearl River, N.Y. as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, reffinose, rhamnose, sucrose and xylose. Cellulose is not utilized.

The reactions of LL-E19020 in the Gordon physiological series are compared in the following Table I with those of *Streptomyces lydicus* ISP 5461 which it most closely resembles morphologically and physiologically.

Because LL-E19020 differs from ISP 5461 in five(5) characteristics (xanthine hydrolysis, decarboxylation of oxalate, acid from erythritol, rhamnose and β-methyl-D-xyloside) it is designated as a subspecies of *Strentomyces lydicus*.

TABLE I

Gordon Test Reactions Of LL-E19020 And *Streptomyces lydicus* ISP 5461

| Reactions | LL-E19020 | ISP 5461 |
|---|---|---|
| Degradation/Transformation of | | |
| Casin | + | + |
| Xanthine | − | + |
| Hypoxanthine | + | + |
| Tyrosine | + | + |
| Adenine | + | + |
| Production of | | |
| Amylase | + | + |
| Gelatinase | + | + |
| Phosphatase | + | + |
| Nitrate Reductase | − | − |
| Urease | + | + |
| Esculinase | + | + |
| Growth on/in | | |
| 5% Sodium chloride | + | + |
| Salicylate | − | − |
| Lysozyme Broth | trace | trace |
| Utilization of | | |
| Acetate | + | + |
| Benzoate | + | + |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |

TABLE I-continued

Gordon Test Reactions Of LL-E19020
And *Streptomyces lydicus* ISP 5461

| Reactions | LL-E19020 | ISP 5461 |
|---|---|---|
| Tartrate | − | − |
| Growth at | | |
| 10° C. | + | + |
| 42° C. | − | − |
| 50° C. | − | − |
| Acid from | | |
| Adonitol | + | + |
| Arbinose | + | + |
| Cellobiose | + | + |
| Dextrin | + | + |
| Dulcitol | − | − |
| Erythritol | + | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Methyl-D-Glucoside | + | + |
| Raffinose | + | + |
| Rhamnose | + | − |
| Salicin | + | + |
| Sobitol | + | + |
| Sucrose | + | + |
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure of X-radiation, ultraviolet radiation, N'-methyl-N'-nitro-N-nitrosoguanidine, actinophages and the like.

Cultivation of *Streptomyces lydicus* SSP. *tanzanius* NRRL 18036 may be carried out in a wide variety of liquid culture media. Media which are useful for the production of LL-E19020 Gamma include an assimilable source of carbon, such as dextrin, sucrose, molasses, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

The antibiotic LL-E19020 Gamma is recovered from the fermentation broth by extraction of the broth into a solvent such as ethyl acetate, followed by chromatography of the ethyl acetate extracted broth using a high pressure liquid chromatography with a twelve (12) liter reverse phase column (C18 bonded phase 40 micron) using 0.1M ammonium acetate pH 4.3/acetonitrile (1:1) to obtain a mixture of LL-E19020 Alpha and LL-E19020 Gamma. Additional purification of this mixture by high pressure liquid chromatography using a twelve (12) liter reverse-phase column (C18 bonded phase 40 micron) using 0.1M ammonium acetate pH 4.3/acetonitrile (1:1) gives pure LL-E19020 Gamma and pure LL-E19020 Alpha.

EXAMPLE 1

Inoculum Preparation

A typical medium used to grow the primary inoculum is prepared according to the following formula:

| | |
|---|---|
| Dextrose | 1.0% |
| Dextrin | 2.0% |
| Yeast extract | 0.5% |
| NZ Amine A | 0.5% |
| Calcium carbonate | 0.1% |
| Antifoam | 0.3% |
| Water qs | 100.0% |

NOTE:NZ Amine A is a pancreatic digest of casein, registered trademark of Scheffield Chemical, Norwich, N.Y.

This medium is sterilized and 100 ml, in a 500 ml flask, is inoculated with *Streptomyces lydicus*ssp. *tanzanius* NRRL 18036. The medium is then placed on a rotary shaker and incubated at 28° C. for 48 hours providing a primary inoculum. This primary inoculum is the used to inoculate 10 liters of the same sterile medium in a bottle. This culture is grown for 24 hours providing secondary inoculum. This secondary inoculum is then used to inoculate 300 liters of the same sterile medium in a tank. This culture is grown at 300° C. for 44 hours with a sterile air flow of 0.66 liters per liter of mash per minute and agitation by an impeller driven at 200 rpm, providing a tertiary inoculum.

EXAMPLE 2

Fermentation

A fermentation production medium of the following formulation is prepared:

| | |
|---|---|
| Dextrin | 7.0% |
| Dextrose | 0.5% |
| Soy flour | 1.5% |
| Corn Steep liquor | 0.5% |
| Calcium carbonate | 0.5% |
| Silicone antifoam | 0.3% |
| Water qs | 100.0% |

This medium is sterilized and 1500 liters is then inoculated with 150 liters of tertiary inoculum from Example 1. The fermentation is conducted at 28° C. with a sterile air flow of 3.3 liters of air per liter of mash per minute and agitation by an impeller driven at 100 rpm for 123 hours, at which time the mash is harvested.

EXAMPLE 3

A fermentation medium of the following formulation is prepared:

| | |
|---|---|
| Dextrin | 7.0% |
| Dextrose | 0.5% |
| Soy flour | 1.5% |

| | |
|---|---|
| Corn Steep Liquor | 0.5% |
| Calcium carbonate | 0.5% |
| Silicone antifoam | 0.3% |
| Water qs | 100.0% |

This medium is sterilized and 3000 liters is then inoculated with 300 liters of tertiary inoculum similarly prepared as in Example 1. The fermentation is conducted at 28° C. with a sterile air flow of 6.5 liters of air per liter of mash per minute and agitation by an impeller driven at 100 rpm for 89 hours, at which time the mash is harvested.

EXAMPLE 4

Isolation and Purification of LL-E19020 Gamma

The harvest mash from two (2) fermentations conducted as described in Example 2 and Example 3, making a total volume of 3200 liters, is diluted with 1600 liters of methyl alcohol and filtered through diatomaceous earth. The filter cake is washed with 320 liters of water and the wash is added to the filtrate giving a total volume of 5000 liters. A 800 liter volume is charged to a still and evaporated to 500 liters. This procedure is repeated until the total volume is reduced to 2950 liters followed by dilution with 1450 liters of ethyl acetate. The lower phase is removed and the upper phase of 900 liters evaporated to 79.5 liters. This concentrate is diluted with 80 liters of ethyl acetate and the lower layer removed. The upper layer is evaporated to give 2.4 liters of a syrup. This crude product is repeatedly decanted with hexane then dissolved in methyl alcohol and applied portion wise to a 12 liter reverse phase column (C18 bonded phase 40 micron). In a typical run, 400 ml of syrup is dissolved in methyl alcohol to give a final volume of 700 ml which is applied to the reverse phase column and eluted with 1:1 0.1M ammonium acetate:acetonitrile at pH 4.3 to afford upon evaporation of the volatiles 38 g of impure LL-E19020 Gamma. Several like runs are completed in this manner and the products combined.

Purification of LL-E19020 Alpha and LL-E19020 Gamma

A total of 100 g of impure LL-E19020 Gamma is charged to a 12 liter reverse phase column (C18 bonded phase 40 micron) and eluted with 0.1M ammonium acetate buffer pH 4.3/acetonitrile (1:1). Fractions designated F1-F28, each having a volume of 20 liters are collected. Fraction F4 is stirred with 15 liters of methylene chloride for 1 hour. The methylene chloride layer is separated and evaporated to 1 liter, dried with calcium chloride and evaporated to a residue which is dissolved in 75 ml of methyl alcohol and filtered. The filtrate is added, 5 ml at a time, to a 2.2×25 cm(10 micron) reverse phase C18 chromatographic column. The column is eluted with 40% acetonitrile in 0.05M ammonium acetate buffer (pH 4.5) at a flow rate of 9.9 ml/minute. The eluate collected after 2.5 to 3 hours is extracted with ethyl acetate. The organic layer is evaporated to a syrup which is dissolved in t-butanol and freeze dried to afford 160 mg of pure LL-E19020 Gamma.

ANALYTICAL HIGH PRESSURE LIQUID CHROMATOGRAPHY (HPLC)

The LL-E19020 Gamma component is analyzed using two different analytical HPLC systems. Retention time compared to E19020 α and β are given in the table below.

| | RETENTION TIME (MINUTES) | |
|---|---|---|
| COMPONENTS | SYSTEM A | SYSTEM B |
| LL-E19020α | 22.7 | 23.5 |
| LL-E19020β | 27.6 | 26.7 |
| LL-E19020γ | 18.5 | 19.6 |

A. HPLC system:Alltech adsorbosphere HS $5\mu$ C18 column (4.6×250mm) with guard column, eluted with a gradient of acetonitrile in 1% aqueous acetic acid. The starting composition is 40% acetonitrile linearly increasing to 70% over 25 minutes and holding at 70% for 5 minutes. The flow rate is 1.0 mL per minute.

B. HPLC system:Alltech adsorbosphere HS $5\mu$ C18 (4.6× 250 mm) with guard column, eluted with a gradient of dioxane in 1% aqueous acetic acid. The starting composition is 55% dioxane, increasing to 70% over 25 minutes and holding at 70% for 5 minutes. The flow rate is 1.0 mL per minutes.

EXAMPLE 5

In Vitro Antibacterial Activity Of LL-E19020 Gamma

The in vitro antibacterial activity of LL-E19020 Gamma is determined against a spectrum of gram positive and gram negative bacteria by a standard agar dilution method. Mueller-Hinton agar containing 5% sheep blood and two-fold decreasing concentrations of LL-E19020 Gamma is poured into petri dishes. The agar surfaces are inoculated with 1 to $5 \times 10^4$ colony forming units of bacteria by means of the Steers replicating device. The lowest concentration of antibiotic that inhibits growth of a bacterial strain after 18 hours incubation is recorded as the minimal inhibitory concentration for that strain.

Minimum Inhibitory Concentration Procedure By Agar Dilution

1. Serial two-flow dilutions of drug are prepared in Mueller-Hinton broth in a range of 2560 $\mu$g/ml-0.15 $\mu$g/ml plus a solvent control.

2. Two milliliters of drug dilution (10X) are added to sterile screw cap bottles to which 18 ml of Mueller-Hinton agar containing 5.6% defibrinated sheep blood is added. Final drug concentration ranges 256 $\mu$g/ml-0.015 $\mu$g/ml in agar containing 5% sheep blood.

3. A few isolated colonies of each test organism are inoculated into 5 ml trypticase soy broth or brain heart infusion broth. The cultures are shaken at 35° C. for 5 hours.

4. Each culture is diluted 1:50 ($10^{-1.7}$) in Mueller-Hinton broth and applied to agar plates using a Steers replicator. Control plates should be seeded last to ensure that viable organisms are present throughout the procedure. Inoculated agar plates are allowed to stand undisturbed until the inoculum spots are completely absorbed.

5. The plates are inverted and incubated at 35° C. for 18 hours with $CO_2$.

6. The minimum inhibitory concentration (MIC) is taken as the lowest concentration of antimicrobial agent at which complete inhibition of antimicrobial agent at which complete inhibition occurs. A very fine, barely visible haze or a single colony is disregarded.

The results are as follows:

In Vitro Activity of LL-E19020 Gamma
MINIMAL INHIBITORY CONCENTRATION (MCG/ML)

| ORGANISM | LL-E19020 GAMMA |
|---|---|
| 1. *Staphylococcus aureus* NEMC 87-69 | 32 |
| 2. *Staphylococcus aureus* ROSE (MP)* | 32 |
| 3. *Staphylococcus aureus* IVES 160 | 32 |
| 4. *Staphylococcus aureus* IVES 396 | 64 |
| 5. *Staphylococcus aureus* VGH 84-47 | 64 |
| 6. *Staphylococcus aureus* CMC 83-131 | 64 |
| 7. *Staphylococcus aureus* SMITH (MP) | 128 |
| 8. *Staphylococcus aureus* ATCC 25923 | >128 |
| 9. *Staphylococcus aureus* ATCC 29213 | 128 |
| 10. *Staphylococcus haemolyticus* AVAH 88-1 | 64 |
| 11. *Staphylococcus haemolyticus* AVAH 88-3 | 16 |
| 12. *Staphylococcus eidermidis* IVES 455 | 16 |
| 13. *Enterococcus spp.* ARUM 87-41 | 8 |
| 14. *Enterococcus spp.* CHBM 88-60 | 16 |
| 15. *Enterococcus spp.* WRVA 88-33 | 16 |
| 16. *Enterococcus spp.* UCI 85-30 | 16 |
| 17. *Enterococcus spp.* VGH 84-69 | 16 |
| 18. *Enterococcus spp.* CMC 83-120 | 16 |
| 19. *Streptococcus pyogenes* AMCH 88-84 | 0.12 |
| 20. *Streptococcus pyogenes* AMCH 88-86 | 0.5 |
| 21. *Streptococcus pyogenes* C203 (MP) | 0.12 |
| 22. *Streptococcus pneumoniae* SV-1 (MP) | 0.12 |
| 23. *Streptococcus pneumoniae* CHBM 88-75 | 16 |
| 24. *Streptococcus pneumoniae* TEX 85-2 | 0.5 |
| 25. *Bacillus cereus* DAVIES | 32 |
| 26. *Klebsiella pneumoniae* NEMC 87-271 | >128 |
| 27. *Escherichia coli* ATCC 25922 | >128 |
| 28. *Escherichia coli* ATCC 35218 | >128 |
| 29. *Pseudomonas aeruginosa* 12-4-4 (MP) | >128 |

*MP = Mouse passage used in in vivo studies

As can be seen from the in vitro data above, LL-E19020 Gamma demonstrated no gram-negative activity (MIC >128 µg/ml), showed poor to moderate activity vs staphylococci and enterococci (MIC 8-128 µg/ml) and relatively good activity against non-enterococcal streptococci (MIC 0.12-16 µg/ml).

EXAMPLE 6

In Vivo Activity Of LL-E19020 Gamma

The in vivo antibacterial activity of antibiotic LL-E19020 Gamma is established by infecting female CD-1 mice from Charles River Laboratories, weighing 20±2 g each, intraperitoneally with either 2.0 ×10 CFU/0.5 ml Streptococcus pyogenes C203 suspended in broth or 2.8×106 CFU/0.5 ml Straphylococcus aureus Smith suspended in 5% hog gastric mucin. The mice were treated subcutaneously, 30 minutes after infection with the indicated dose of the test compound in 0.5 ml of 0.2% aqueous agar. Toxicity studies were performed administering the same treatment to uninfected mice.
The results are as follows:

In Vivo Activity Of LL-E19020 Gamma
Survival Ratio 7 Days After Infection With

| Single Subcutaneous Dose (MG/KG) | *S. pyogenes* C203 LL-E19020 Gamma | *S. aureus* Smith LL-E19020 Gamma |
|---|---|---|
| 64 | NT | 0/5 |
| 32 | NT | 0/5 |
| 16 | 4/5 | 0/5 |
| 8 | 3/5 | 0/5 |
| 4 | 1/5 | 0/5 |
| 2 | 0/5 | 0/5 |
| 1 | 0/5 | 0/5 |
| 0.5 | 0/5 | 0/5 |

| Single Subcutaneous Dose (MG/KG) | LL-E19020 Gamma |
|---|---|
| 64 | 2/2 |
| 32 | 2/2 |
| 16 | 2/2 |
| 8 | 2/2 |
| 4 | 2/2 |
| 2 | 2/2 |
| 1 | 2/2 |
| 0.5 | 2/2 |

The data above shows the in vivo activity of LL-E19020 gamma vs acute lethal infections in mice. LL-E19020 gamma had an approximate $ED_{50}$ between 4–8 mg/kg/ssc vs *Streptococcus pyogenes* C203. Against the *Staphylococcus aureus* Smith infection LL-E19020 gamma had an approximate $ED_{50}$ of >64 mg/kg/ssc. LL-E19020 gamma did not exhibit toxic symptoms when dosed subcutaneously at the same levels used in the protection study.

Antibiotic LL-E19020 Gamma derives its utility from antibacterial activity. For example this antibiotic may be used in the suppression of bacterial infections, as a topical antibacterial agent and as a general disinfectant for laboratories.

In addition to its antibacterial activity this compound is effective as an anticoccidial agent in poultry and as a growth promotant and anthelmintic agent. These utilities are the subject of patent applications filed concurrently herewith and incorporated herein by reference.

In therapeutic use, the compound of this invention may be administered in the form of a conventional pharmaceutical composition appropriate for the intended use. Such a composition may be formulated so as to be suitable for oral, parenteral, or topical administration. The active ingredient may be combined in admixture with a nontoxic pharmaceutically acceptable carrier, which carrier may take a wide variety of forms depending on the form of preparation desired for administration, ie, oral, parenteral or topical.

When the compound is employed for the above utility, it can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

An effective amount of compound from 0.2 mg/kg of body weight to 100.0 mg/kg of body weight should be administered one to five times per day via any topical route of administration including but not limited to oral, parenteral (including subcutaneous, intravenous, intramuscular, intrasternal injection or infusion techniques), by inhalation spray, or rectally, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compound is preferred.

These active compounds may also be administered parenterally or intraperitoneally. Solutions or suspensions of these active compounds as a free base or pharmacologically acceptable salt can be prepared in water suitably mixed with a surfactant such as hydroxy propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil.

We claim:
1. A compound LL-E19020 Gamma comprising
(a) the structure

(b) an elemental analysis:C 62.22; H 7.77; N 0.92;
(c) a molecular weight of 1241 (FABMS=M/Z 1264 corresponding to [M+Na]+);
(d) a specific optical rotation: $[\alpha]_D 26°$ C.=−7° C.(1.001, MeOH)
(e) a characteristic ultraviolet absorption spectrum as shown in FIG. I of the attached drawings;
(f) a characteristic infrared absorption spectrum as shown in Figure II of the attached drawings;
(g) a characteristic proton nuclear magnetic resonance spectrum as shown in Figure III of the attached drawings;
(h) a characteristic carbon-13 nuclear magnetic resonance spectrum as shown in Figure IV of the attached drawings,
(i) a characteristic HPLC retention time of 18.5 minutes using a gradient of acetonitrile in aqueous acetic acid; and
(j) a characteristic HPLC retention time of 19.6 minutes using a gradient of dioxane in aqueous acetic acid.

2. A method of treating bacterial infections in warm blooded animals which comprises administering to said animals an antibacterially effective amount of antibiotic LL-E19020 Gamma as defined in claim 1.

3. A antibiotic pharmaceutical composition which comprises an antibiotic amount of LL-E19020 Gamma as defined in claim 1 in association with a pharmaceutically acceptable carrier.

* * * * *

UNITED STATES PATENT AND TRADEMARK OFFICE
CERTIFICATE OF CORRECTION

PATENT NO.   : 5,814,613
DATED        : September 29, 1998
INVENTOR(S)  : Guy Thomas Carter, David R. Williams and Joseph D. Korshalla It is certified that error appears in the above-identified patent and that said Letters Patent is hereby corrected as shown below:

Column 12, Claim 1, line 34, delete "26° C.=-7° C." and insert -- 26° =-7° --

Signed and Sealed this

Twenty-third Day of February, 1999

Attest:

Q. TODD DICKINSON

*Attesting Officer*   *Acting Commissioner of Patents and Trademarks*